US007934411B2

(12) United States Patent
Koch

(10) Patent No.: US 7,934,411 B2
(45) Date of Patent: May 3, 2011

(54) GAS OR HEAT DETECTOR, GAS OR HEAT GENERATOR, SMOKE GAS GENERATOR, AND METHOD FOR THE TESTING OF A GAS DETECTOR OR A HEAT DETECTOR AND METHOD FOR THE TESTING OF A SMOKE GAS DETECTOR

(75) Inventor: Hubert Koch, Mönchengladbach (DE)

(73) Assignee: Tormaxx GmbH, Mönchengladbach (DE)

( * ) Notice: Subject to any disclaimer, the term of this patent is extended or adjusted under 35 U.S.C. 154(b) by 539 days.

(21) Appl. No.: 11/142,042

(22) Filed: Jun. 1, 2005

(65) Prior Publication Data
US 2005/0204799 A1  Sep. 22, 2005

Related U.S. Application Data

(63) Continuation of application No. 10/381,901, filed as application No. PCT/DE01/03747 on Oct. 1, 2001, now abandoned.

(60) Provisional application No. 60/289,872, filed on May 9, 2001, provisional application No. 60/290,133, filed on May 10, 2001, provisional application No. 60/291,880, filed on May 18, 2001.

(51) Int. Cl.
*G01N 21/00* (2006.01)

(52) U.S. Cl. .......................... 73/1.03; 73/1.06

(58) Field of Classification Search ........... 73/1.03–1.06
See application file for complete search history.

(56) References Cited

U.S. PATENT DOCUMENTS

| 4,271,693 | A | | 6/1981 | Bute | |
|---|---|---|---|---|---|
| 4,489,590 | A | * | 12/1984 | Hadden | 73/1.04 |
| 4,741,717 | A | | 5/1988 | Wolf | |
| 5,522,229 | A | * | 6/1996 | Stuchlik et al. | 62/127 |
| 5,670,946 | A | * | 9/1997 | Ellwood et al. | 340/628 |
| 5,917,417 | A | * | 6/1999 | Girling et al. | 340/628 |
| 6,124,795 | A | * | 9/2000 | Bernau et al. | 340/628 |
| 6,282,940 | B1 | | 9/2001 | Hung et al. | |
| 6,619,594 | B2 | | 9/2003 | Wolf et al. | |
| 6,632,674 | B1 | * | 10/2003 | Warburton | 436/8 |
| 6,732,796 | B2 | * | 5/2004 | Vinegar et al. | 166/259 |

FOREIGN PATENT DOCUMENTS

| CA | 2 083 990 | 5/1994 |
|---|---|---|
| GB | 2 176 600 | 12/1986 |

OTHER PUBLICATIONS

English translation of Chinese Office Action dated Apr. 7, 2010.

* cited by examiner

*Primary Examiner* — Robert R Raevis
(74) *Attorney, Agent, or Firm* — Collard & Roe, P.C.

(57) ABSTRACT

Inspecting gas detectors is difficult if the gas detectors are arranged in a place which is difficult to access. The provision of a test device which is in an operational connection with the gas detector or the heat detector facilitates the testing considerably.

43 Claims, 7 Drawing Sheets

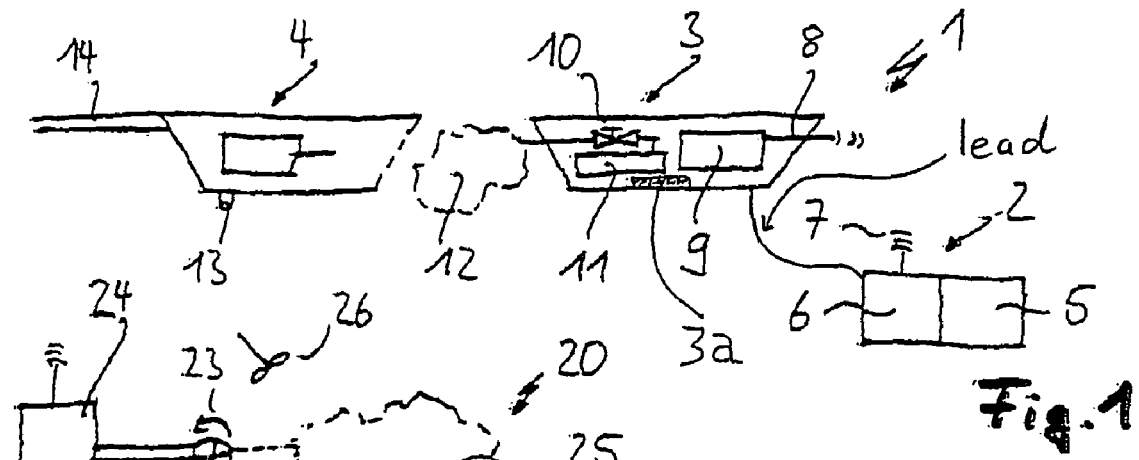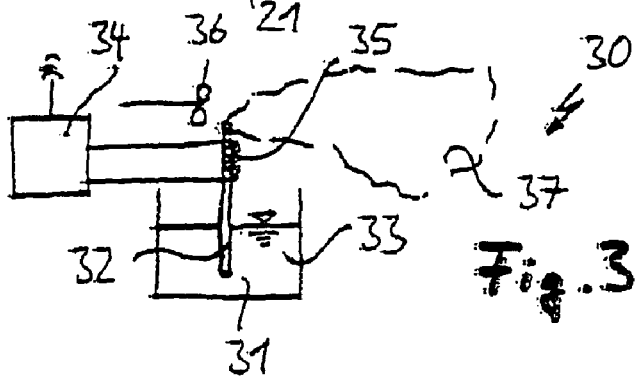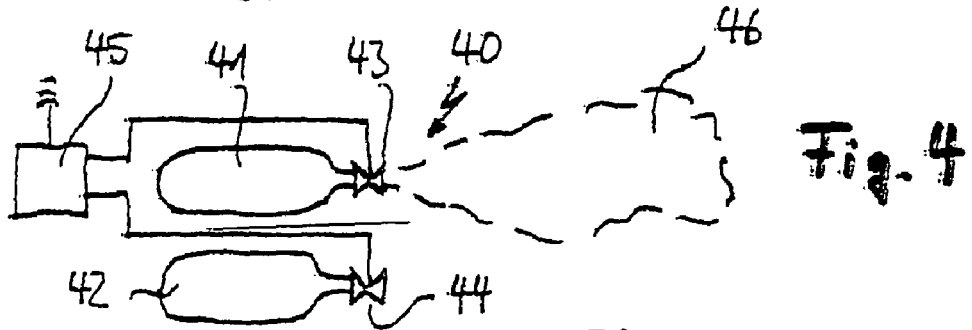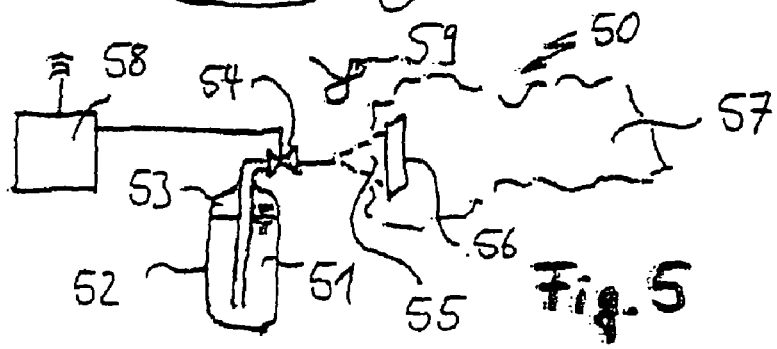

Figure 6:
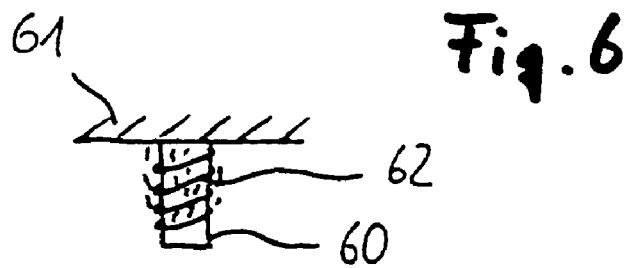

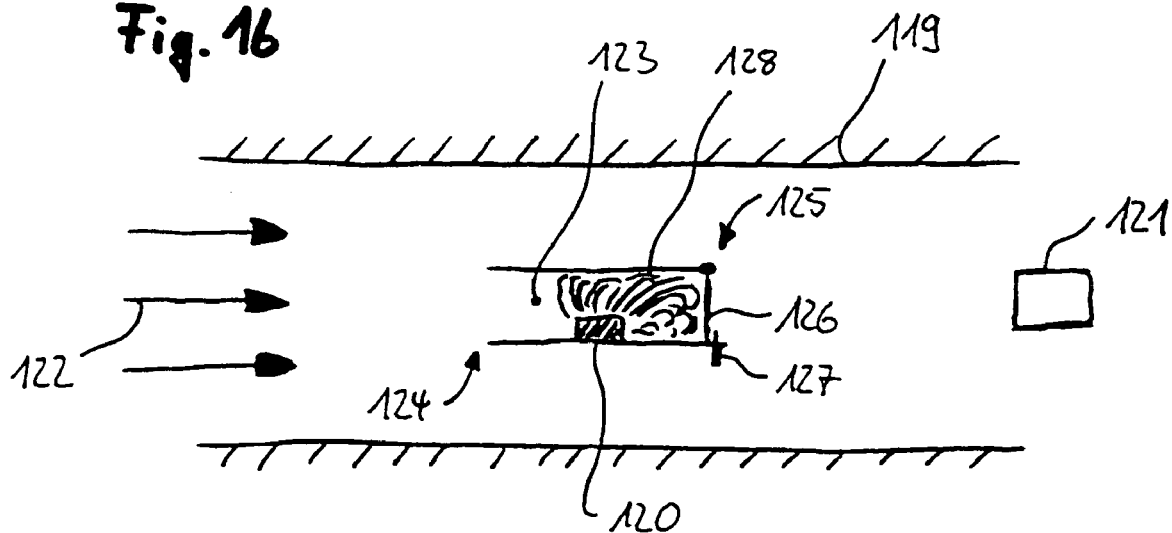
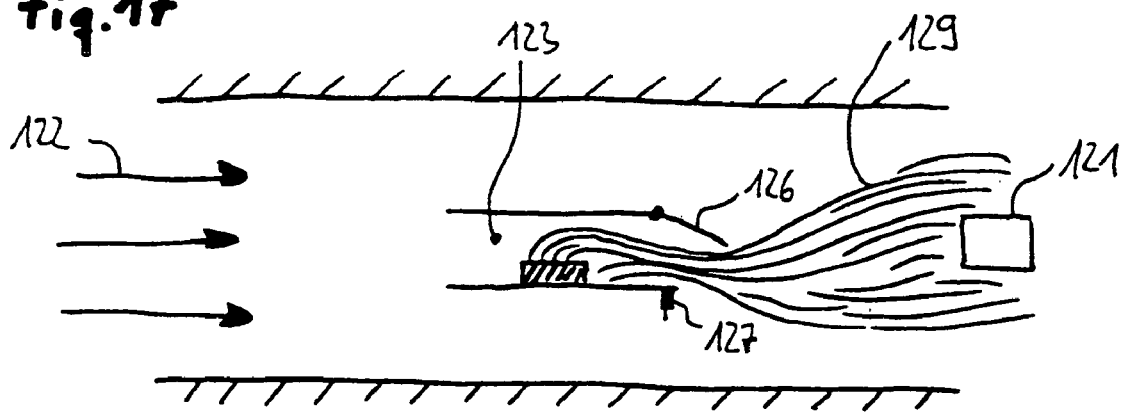
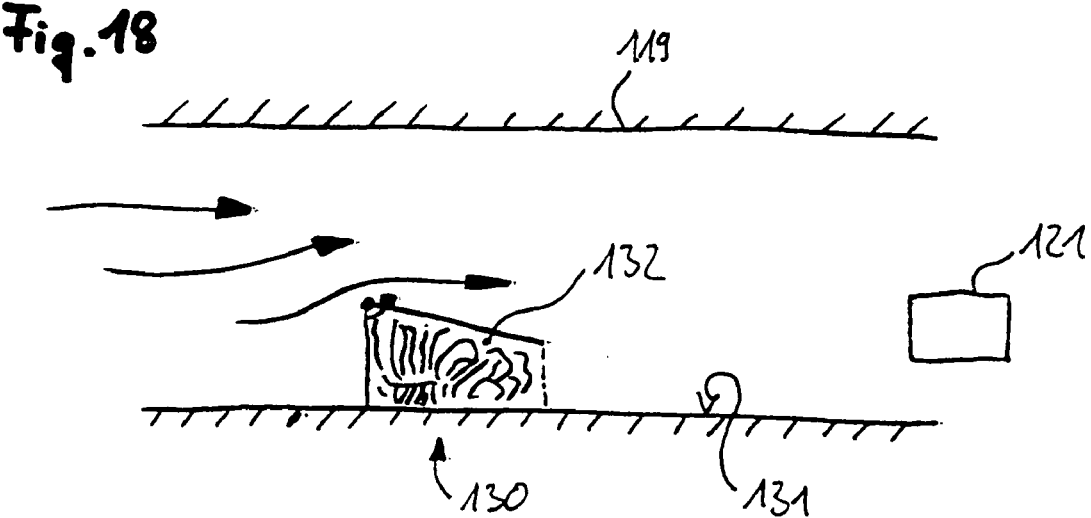

GAS OR HEAT DETECTOR, GAS OR HEAT GENERATOR, SMOKE GAS GENERATOR, AND METHOD FOR THE TESTING OF A GAS DETECTOR OR A HEAT DETECTOR AND METHOD FOR THE TESTING OF A SMOKE GAS DETECTOR

CROSS REFERENCE TO RELATED APPLICATIONS

This application is a continuation and claims priority under 35 U.S.C. §120 of U.S. patent application Ser. No. 10/381,901 filed Jun. 30, 2003, now abandoned which claims the benefit as a National Stage entry of a PCT application pursuant to 35 U.S.C. §371 of International Application No. PCT/DE01/03747 filed Oct. 1, 2001, published in the German language, which in turn claims priority under 35 U.S.C. §119 of German Application No. 100 48 760.2, filed Sept. 29, 2000; German Application No. 101 04 330.9, filed Jan. 30, 2001; German Application No. 101 17 469.1, filed Apr. 6, 2001; German Application No. 101 22 572.5, filed May 9, 2001; U.S. Provisional Application No. 60/289,872, filed May 9, 2001; U.S. Application Provisional No. 60/290,133, filed May 10, 2001; U.S. Provisional Application No. 60/291,880, filed May 18, 2001; and German Application No. 101 39 033.5, filed Aug. 15, 2001. Applicant also claims priority under 35 U.S.C. §365 of PCT/DE01/03747, filed Oct. 1, 2001. The international application under PCT article 21(2) was not published in English.

The invention relates to a gas or heat detector, a gas generator or heat generator in particular for a gas detector or heat detector, and a smoke gas generator, for preference for the simulation of real smoke gas, and a method for the testing of a gas detector or a heat detector and a method for the testing of a smoke gas detector, in which a smoke gas generator arranged in the vicinity of the smoke gas detector generates the smoke gas by means of a test medium and in which the smoke gas initiates a test of the smoke gas detector.

Gas detectors and heat detectors, in particular smoke gas detectors, serve to detect air contamination due to special gases in buildings, or the heat engendered by fire, and to issue a signal. This signal can be a visual or audible signal. For preference this signal is used to activate a mechanism which counteracts the presence of the smoke gas, and the spread of smoke gas or fire. Mention may be made in this context of roller doors, which close in such situations in order, for example, to prevent the spread of fire.

Gas detectors of this kind, in particular smoke gas detectors and/or heat detectors, are usually attached to the ceiling of the building, since the smoke gases and/or the heat collect as a rule at the ceiling and can so allow for the rapid detection of the smoke gas or fire which is present. In larger halls in particular, such as at airports or concert halls, a large number of gas detectors and heat detectors are arranged on the ceiling, and are connected by electric leads to a smoke gas detector system which provides for the actuation of the correct mechanisms, such as the closing of doors or the operation of a sprinkler system.

Such systems have reached a high technical standard, and are highly reliable in their function. Despite this, it is specified by regulations that these systems be examined at regular intervals, in order that, among other things, defective gas detectors can be replaced. To do this, the gas detectors are connected to an artificially created gas, in particular an artificially created smoke gas, so that this initiates an alarm which causes the reaction provided for either directly or via a smoke gas detector system. At airports, for example, the blowing of smoke at a gas detector can cause the closure of a roller door.

The arrangement of the gas detectors in the ceiling area leads to problems in particular if extremely high ceiling heights are involved and the gas detectors are difficult to access as a result. Even with lower ceiling heights, the problem frequently arises that the gas detectors are arranged behind cladding, and are therefore difficult to access.

In order to inspect smoke gas detectors in particular with regard to their functional efficiency, mobile smoke gas generators in particular are known. These smoke gas generators are held on a smoke gas detector until the smoke gas artificially generated by this actuates an alarm.

This involved devices which conduct a test aerosol in a pressure cylinder. A disadvantage with these devices is that, among other things, the pressure cylinder makes them difficult to handle. Likewise, the actuation of such a device is difficult to carry out due to an actuation mechanism which in most cases is complicated and elaborate.

A further generic type of test device is known from the company of Hekatron GmbH. This test device used a smoke bar for the generation of smoke gas, which is inserted into a housing on the device, whereby the housing must be closed again with great care, since it is important to ensure that a sealing ring which seals a floor or the upper part of the housing is not damaged. During the actual testing of the smoke gas detector, a hose tip of the testing device is then held at the smoke gas detector, whereby the smoke gas must be expelled by the compression of a rubber ball out of the hose tip and onto the smoke gas detector. In addition to the unwieldy handling described heretofore, during a pump cycle an air ventilation hole of the housing must be closed by means of a finger, so that no smoke gas can escape from this air ventilation hole during the compression of the rubber ball. In order to fill the compressed rubber ball with air again, the air ventilation hole of the housing is cleared, so that fresh air can flow through it into the rubber ball of the test device. Such a method is extremely unwieldy if the smoke gas detector which is to be tested is suspended high on the ceiling.

Known testing devices for gas detectors or heat detectors in most cases have, as described, a considerably complicated method of operation. Added to this is the fact that the test procedure with the known testing devices not infrequently must be carried out several times because of frequent failed attempts. Another disadvantage in this situation is that, due to the prolonged presence of the test aerosols or of the smoke from the smoke bar in or at the smoke detector, long waiting times are incurred before the smoke gas detector is reset from an alarm state into a normal state.

The invention is based on the problem of further developing fire detection systems, in particular gas detection and heat detection systems, in such a way that they can be more easily examined.

This problem is resolved on the one hand by a gas detector or heat detector exhibiting a test device which is in operational connection with the gas detector or heat detector.

The term "gas" is understood in this situation to mean all gaseous media, such as, for example, also gases which exhibit solid particles.

This accordingly also includes all smoke gases which exhibit solid particles, so that, as a result, smoke gas detectors can also be addressed which are have been created in order to detect a smoke gas.

It is of particular advantage if the test device comprises a gas generator and/or a heat generator. As a result of this, it is possible to impose appropriate preconditions on the test device for testing a gas detector or heat detector. It is understood that the test device for a gas detector exhibits for preference a gas generator and the test device for a heat detector for preference exhibits a heat detector. Depending on the application situation, it may be sensible for a test device to comprise a gas generator and a heat generator.

It is understood that the generation of a smoke gas with solid particles can also be replaced by the generation of a gas without solid particles. This is an advantage in particular if it is intended to test the function of a gas detector which responds to the presence of a gas which is free of solid particles.

It is further understood that the terms "gas detector" and "gas generator" likewise implies all technical devices which can detect or generate a smoke gas. This means that the term "gas detector" also implies a smoke gas detector and the term "gas generator" also implies a smoke gas detector.

The invention is based on the realisation that a gas generator can be provided for at least one gas detector. This gas generator can then be arranged in the vicinity of the gas detector. By the actuation of the gas generator a smoke gas is produced, for example, which will be detected by the gas detector so that it issues a signal. The gas generator can, for example, be arranged as stationary on building ceilings. For example, the gas generator is allocated to a special gas detector by means of individual positioning, so that the gas generator can be fixed in any desired position in relation to the gas detector.

It is also possible, however, for the gas generator and the gas detector to form one physical unit. This is particularly advantageous, for example, if only a limited structural space is available for the locating of a gas detector and a gas generator, or if special regulations in respect of a supervisory authority must be maintained.

The system according to the invention, consisting of a gas detector and a gas generator, in particular of a smoke gas detector and a smoke gas generator, does indeed lead to a situation in which a large number of smoke gas generators are required in comparison with the prior art. However, because the smoke gas generators no longer have to be conducted to the gas detector when the system is tested, but can be installed as stationary, a high costs advantage is incurred, as a rule, for the operator of the system. While hitherto ladders needed to be used in order to bring a smoke gas generator to a special gas detector, or claddings had to be removed in an elaborate and expensive manner, it is sufficient, with one single installation of the smoke gas generator in each case in the vicinity of a gas detector, for the smoke gas generator to be actuated once in order to test the gas detector allocated to it.

Only if it should happen that the interplay of gas generator and gas detector does not function, and of smoke gas generator and smoke gas detector in particular, does the technician need to examine the system. If the interplay is functioning, however, it will be ensured that the gas detector is in order and further examinations are, to advantage, therefore superfluous.

Because with regular examinations of the gas detectors it is found, as a rule, that the detectors are in good order, and individual units only need to be replaced in exceptional cases, the gas detectors according to the invention facilitate the work of the service company and so lead to a considerable costs advantage for the system operator.

Simple re-equipping of systems with the gas detector according to the invention is achieved in that a gas generator is arranged next to the known gas detectors used hitherto. As a result, a gas detector according to the invention is achieved, with which the gas generator is arranged for preference immediately next to the gas detector. The gas generator can, for example, be screwed to the ceiling next to the gas detector as a simple component in existing buildings equipped with gas detectors. This leads to an economical re-equipping of existing systems, and therefore immediately to a reduction in the maintenance expenditure without high investment costs.

It is proposed for new systems in particular that the gas generator be integrated in the gas detector. This results in the creation of a simple and compact system, which provides both the gas monitoring system as well as the actual control system. The integration of gas generator and gas detector further leads to the advantage that system components of the gas detector, such as, for example, the power supply, can also be used for the gas generator.

Because gas detection systems, and smoke gas generators in particular, must be inspected at regular intervals, it is proposed that the gas detector should exhibit a time clock. The time clock allows for the gas detector to be pre-programmed to be tested at regular intervals of time, in that, at predetermined times, a smoke gas is emitted by the smoke generator, for example, which necessarily leads to the predetermined reaction at the gas detector. If the predetermined reaction is not caused, a more precise examination of the gas detector and, if appropriate, of the gas generator will be necessary.

An advantageous alternative embodiment makes provision for the gas generator to exhibit a remote control. A remote control of this type can be implemented by means of leads or without cables, and allows for the gas generator to be actuated at any desired times. As a rule, this serves for the gas detector to be tested. The remote control can also serve, however, to bring about the reaction initiated by the gas detector. For example, a roller door can be closed by means of this remote control in that a smoke gas is generated which takes effect on the gas detector and therefore actuates the closure of the roller door.

It is to advantage if the gas generator is capable of actuation electrically. For this purpose the gas generator can be provided with a power supply, to which current is then applied if it is intended, for example, that smoke gas is to be generated.

One variant embodiment makes provision for the gas generator to be designed as a component which is independent of electric current. The energy which is necessary for the smoke generation or smoke gas release is in this case provided by a battery, which for preference is rechargeable. Gas generators of this type, as wireless remote-controlled elements, can be easily installed and easily operated.

The person skilled in the art is aware that there are various possibilities of generating the smoke gases required, depending on the application situation.

One simple embodiment variant makes provision for the gas generator to exhibit a gas cartridge. This gas cartridge is filled with a smoke gas which is under pressure, so that, when the gas cartridge is opened, smoke gas is released for as long as the cartridge remains open. The gas cartridge can be filled with different types of gas or a gas mixture, and several different -gas cartridges can be arranged in the gas detector, in order to test the response of the gas detector to different types of gas, in particular to a smoke gas.

The heat device in this case ensures that, when the gas generator is actuated, fluid is evaporated and a smoke gas, for example, is released. In this situation it is of advantage if the heat device is only heated when it is intended that the smoke gas should be generated. The fluid container can also be designed as an overpressure container, in such a way that it allows for the fluid to be sprayed. This fluid, in interaction with the heat device, can generate a gas by evaporation or combustion, or the fluid or gas emerging from the fluid container is ignited, so that the heating device generates an appropriate gas or heat by the combustion of the emerging fluid.

In order for the gas created to be conducted specifically to the gas detector, it is proposed that the gas generator exhibit a fan blower. This blower must only be switched off if, for example, smoke gas is being generated. In addition, it is also possible for gas detectors which are temporarily contaminated with smoke gas, for example, to be blown free again after the detection of the smoke gas. This results in the substantial shortening of a test cycle, since the gas detector 4 can be switched back again more rapidly from an alarm state to the normal state.

Because it can be difficult, for example in respect of installation or maintenance work, for cartridges under pressure or containers filled with fluid to be transported, it is proposed that the gas generator exhibits a solid body which evaporates at least in part during heating. This solid body can be a plastic element of a wax. This wax is for preference heated by a resistor element heated by a current passing through it, so that, when the current flows, the heat causes a part of the solid body to evaporate. Such a wax-type solid body can be a water-clear odourless gel. Well-suited for this are gels of hydrocarbons in the white oil range, which are manufactured with the addition of a gel forming agent. Such oils have for preference a boiling point which is above 250° C. The melting point is for preference at about 80° C. This leads to the situation in which, with such substances, practically no evaporation of constituent elements takes place at room temperature. Any burden on the ambient air during the storage of the substances or of the volume located in the test device can therefore be reliably excluded.

In practice, long-chain aliphatic hydrocarbons are used, of which about 1 mg is evaporated per test procedure. This evaporated volume is, not of any relevance with regard to health, since long-chain aliphatic hydrocarbons only lead to mechanical irritation of the upper respiratory passages in high concentrations. The substances described further have the advantage that they settle in the vicinity of the emission of the substance, and the volumes of material released do not lead either to corrosion or to other negative influences on adjacent electronic or mechanical components.

This substance can be used to advantage in particular with all the smoke gas generators described in this Application.

The problem on which the invention is based is resolved on the one hand by a heat detector, in particular a fire detector, exhibiting a heat generator with which it is in operational connection.

The term "heat generator" is to be understood to mean all technical devices with which a degree of heat can be generated which is sufficiently hot to be detected by a heat detector. It is understood that use may be made as heat generators of electrical devices, devices with an open flame, or similar devices for the generation of heat.

In a similar way as described heretofore for the gas detector and the gas generator, it is possible for a heat generator to be provided for at least one heat detector. This heat generator can then likewise be arranged in the vicinity of the heat detector. The heat generator in this situation produces a heat of such a degree that it is detected by the heat detector, so that this issues a signal. The heat generator can in this case be arranged, for example, stationary on building ceilings. Thanks to its freely selectable positioning in each case it is allocated to a special heat detector.

The system according to the invention, of a heat detector, in particular a fire detector, and a heat generator, does indeed lead to a situation in which a large number of heat generators are required in comparison with the prior art. However, because the heat generators no longer have to be brought to the heat detector when the system is tested, but can be installed as stationary, a high costs advantage is incurred, as a rule, for the operator of the system. While hitherto ladders needed to be used in order to bring a heat generator to a special heat detector, or claddings had to be removed in an elaborate and expensive manner, it is sufficient, with one single installation of the heat generator in each case in the vicinity of a heat detector, for the heat generator to be actuated once in order to test the heat detector allocated to it.

Only if it should happen that the interplay of heat generator and heat detector, and of fire detector in particular, does not function, does the technician need to examine the system and repair it if necessary. If the interplay is functioning, however, it will be ensured that the heat detector is in order and further examinations are, to advantage, therefore superfluous.

Because with regular examinations of the heat detectors it is found, as a rule, that the detectors are in good order, and individual units only need to be replaced in exceptional cases, the heat detectors according to the invention facilitate the work of the service company and so lead to a considerable costs advantage for the system operator.

Simple re-equipping of systems with the heat detector according to the invention is achieved in that a heat generator is arranged next to the known heat detectors used hitherto. As a result, a heat detector according to the invention is achieved, with which the heat generator is arranged for preference immediately next to the heat detector. The heat detector can, for example, be screwed to the ceiling next to the heat detector as a simple component in existing buildings equipped with heat detectors. This leads to an economical re-equipping of existing systems, and therefore immediately to a reduction in the maintenance expenditure without high investment costs. It is proposed for new systems in particular that the heat generator be integrated in the heat detector, a fire detector in particular. This results in the creation of a simple and compact system, which provides both the fire monitoring system as well as the actual control system itself. The integration of heat generator and heat detector further leads to the advantage that system components of the heat detector, such as, for example, the power supply, can also be used for the heat generator.

Because heat detection systems must be inspected at regular intervals, it is proposed that the heat detector should exhibit a time clock. The time clock allows for the heat detector to be pre-programmed to be tested at regular intervals of time, in that, at predetermined times, a degree of heat is generated by the heat generator which necessarily leads to the predetermined reaction at the heat detector. If the predetermined reaction is not caused, a more precise examination of the heat detector and, if appropriate, of the heat generator will be necessary.

An advantageous alternative embodiment makes provision for the heat generator to exhibit a remote control. A remote control of this type can be implemented by means of leads or without cables, and allows for the heat generator to be actuated at any desired times. As a rule, this serves for the heat detector to be tested. The remote control can also serve, however, to bring about the reaction initiated by the heat detector. For example, a roller door can be closed by means of this remote control in that a degree of heat is generated which takes effect on the heat detector and therefore actuates the closure of the roller door. It is to advantage if the heat generator can be electrically actuated. The heat generator can be provided with an electricity supply for this purpose, on which current is only imposed if it is intended that heat should be generated.

The person skilled in the art is aware that there are various possibilities of generating the heat required, depending on the application situation. A simple embodiment makes provision for the heat generator to exhibit an electrical heating device. This heating device is arranged, for example, in the vicinity of an appropriately heat sensitive sensor of the heat detector. If a current now flows through a metallic wire of the electrical heating device, the wire will heat up in such a way that the sensor of the heat detector detects this source of heat.

Another embodiment variant makes provision for the heat generator to exhibit a fan blower. For example, a heating device is not arranged directly at a sensor of the heat detector, but at a distance interval from it. In order for the heat now to be brought effectively into the vicinity of the heat detector, the fan blower is switched on when the heating device of the heat generator is active. In this situation, hot air passes to the sensor of the heat detector.

One embodiment variant makes provision for the heat generator to be designed as a component which is independent of electric current. The energy which is necessary for the generation of the heat is produced in this case by a battery which for preference is rechargeable. Such heat generators are in particular easily installable and easy to operate as wireless remote-controlled elements.

One simple embodiment variant makes provision for the heat generator to exhibit a fluid container and an ignition device. The fluid container in this situation contains a combustible medium, which can, for example, flow through a nozzle into the surrounding environment and can be ignited by an ignition device, so that a flame is produced. For example, the heat generator is arranged in such a way that the flame is arranged immediately beneath the heat detector, so that the heat detector is actuated by the rising heat. It is likewise possible for the flame to heat a metal device to which the sensor of the heat detector is allocated such that, when the metal is heated, the heat detector is activated. If, for example, an arrangement of a heating device operated with fluid is not possible in the immediate vicinity of the heat detector, it is also possible in this situation for a fan blower to bring the heat from the flame into the vicinity of the heat detector.

The medium of the fluid container can in this situation be under pressure or pressureless.

A further embodiment variant makes provision for the heat generator to exhibit a solid body, which emits a radiant heat when activated. This is, for example, an infra-red lamp which is arranged in the immediate vicinity of the heat detector, so that, on activation, the radiant heat of the infra-red lamp is sufficient to activate the heat detectors.

The problem on which the invention is based is resolved by a gas generator or heat generator, in particular for a gas detector or heat detector which exhibits a fluid container and a capillary tube, whereby one end of the capillary tube is arranged in the fluid container and the other end exhibits a heating device, and whereby the heating device exhibits a remote control.

A gas generator of this type is especially simple in design and can be integrated either in known gas detectors or arranged next to known gas detectors. The capillary tube conveys a small flow of a fluid to a heating device which, provided it is switched on, provides for the evaporation or vaporisation of the fluid. In order for smoke gas to be generated only at specified times, for example, the heating device exhibits a remote control, by means of which it is adjusted. This simple design of a gas generator shows that with simple means the high expenditure on service incurred with smoke gas detectors in particular can be reduced without safety being prejudiced.

In order to avoid the overheating of the test medium, the possibility pertains of temporarily limiting the heating duration of the heating device, so that a switch needs to be activated accordingly for the renewed activation of the heating device.

A preferred embodiment makes provision for the gas generator to exhibit a heat conducting body. The heat conducting body is manufactured, for example, from an electrically conductive metal plate, so that the heatable surface is raised. In this situation the surface of the metal plate is far larger than the surface of the wire.

It is of particular advantage if the heat conducting body exhibits an electrical resistor. This resistor is, for example, a conventional commercial Ohmic resistor, with the result that a product taken from mass production can be used in order to enhance the performance of the heating device.

According to a further embodiment it is to advantage if the heat conducting body exhibits a porous material. The porosity of the material allows for a further substance to be sucked up in the manner of a sponge, so that the substance is in close contact with the heat conducting body in the area of the pores. If the heat conducting body or the electrical resistor is heated, the substance deposited in the porous material evaporates, as a result of which, for example, a smoke gas is produced.

If the heat conducting body is not itself a porous body, it is of advantage if a porous component is arranged at the heat conducting body. A substance can also be stored in the pores of this porous component.

In order, for example, to achieve smoke gas production at a specific point of the porous component and/or to prevent an uncontrolled emergence of the substance from the porous component, it is to advantage if the porous body or the porous component exhibits a surrounding, for preference a heat-resistant film. Due to the heat-resistant film, the substance heated by the porous component will be prevented from being rendered volatile at an undesired point of the porous component.

To advantage the surrounding has at least one opening. For example, the heat-resistant film exhibits an opening through which the heated substance evaporates or becomes volatile.

An especially preferred embodiment makes provision for the gas generator to -exhibit an interface to a network. For example, the gas generator is connected to a local network of a building, so that the gas generator can be actuated from a central device, for example. The interface can in this situation be both cable-connected as well as cableless. It is likewise possible for the gas generator to exhibit not only a contact to a local network, but, rather, also to a wide area network. For example, a gas generator is connected via a wide area network to a central security service, which is not located directly in the building with the gas detectors which are to be inspected.

It is understood that the heat generators described heretofore can likewise be connected to a network by means of an interface. In this situation, the same advantages pertain as with the gas generator.

The problem on which the invention is based is also resolved by a smoke gas generator for the simulation of a real smoke gas, whereby the smoke gas generator exhibits an electrical heating device for the generation of the smoke gas. Such an electrical heating device can be provided in a wide variety of forms, but particularly preferred is a heat generator which exhibits an electrically conductive wire. The advantage with this heat generator is that a degree of heat can be generated with this without an open flame being used. In order to generate the heat, all that is required is for a current to be conducted through the wire, so that it is heated. An electrical heating device is therefore particularly advantageous.

A preferred embodiment variant makes provision for the heating device to be an electrical resistor. This is for preference a conventional commercial Ohmic resistor, which can be inserted in a simple manner into an electrically conductive wire. On the one hand the Ohmic resistor in particular enhances the heat generation, and, on the other, it increases the surface area which is capable of emitting heat.

It is of particular advantage if the smoke gas generator exhibits an electrical blower unit. The electrical blower unit can in this situation be a small fan which sucks air from the surroundings and then conducts this through the smoke gas generator, whereby the air conducts the air conducts the smoke gas through an aperture of the smoke generator in the direction of a smoke gas detector. It is possible to use any other device which is capable of accelerating air instead of the fan.

A further embodiment variant makes provision for the smoke gas generator to exhibit an electrical energy source. By means of this electrical energy source, for example, a current supply can be guaranteed for the heating device and the blower. As an electrical energy source in this situation a public power network or a solar power unit may be used. For preference, however, the electrical energy source has a battery or a rechargeable accumulator.

It is of particular advantage if the smoke gas generator can be actuated electrically. In this situation smoke gas will only be generated if the heating device or the heat generator is actuated electrically, whereby a current then flows from the electrical energy source through the heating device or through the heat generator respectively.

It is proposed-according to the invention that the smoke gas generator exhibits a heat conducting body. For example, the heat conducting body is manufactured from an electrically conductive metal plate, so that, as a result of the relatively large surface of the metal plate in relation to the surface of the wire, the heatable surface area is increased. It is of particular advantage if the heat conducting body is designed in the form of an electrical resistor. This resistor is, for example, a conventional commercial resistor, with the result that a product from mass production can be drawn upon to enhance the performance of the heating device.

According to a further embodiment variant, provision is made for the smoke gas generator to exhibit a heat chamber in which a test medium is arranged. To advantage the smoke gas is generated by the test medium.

For preference the heating device is arranged in the heat chamber, so that it is located in the immediate vicinity of the test medium.

The test medium can be solid or fluid, and it is to particular advantage if the test medium comprises a gel-type material which at least partially dissolves into smoke during the heating. For example, the electrical heating device or the heat conducting body, in particular the conventional commercial resistor, is located in the gel-type test medium, so that during the heating a part of the test medium is heated to such a degree due to the immediate proximity of the heating device that it evaporates into a gaseous state, and the smoke gas generator creates a smoke gas.

It has been found that it is to advantage if the test medium exhibits a mass of less than 5 g, for preference of less than 1 g. To advantage, the smoke gas generator according to the invention requires only approximately 0.001 g of the gel-type test medium, so that up to 600 tests can be conducted with the smoke gas generator according to the invention without the smoke gas generator being refilled with a test medium. With a monthly test cycle this corresponds to a service life of approximately 40 years. To advantage, the smoke gas generator can be refilled with a new test medium. Due to the small volume of test medium, the weight of the smoke gas generator can be substantially reduced.

According to a further embodiment of the invention provision is made for the heating device to be in operational contact with the test medium. For example, the heating device is arranged in the heat chamber in such a way that it is directly enclosed by the test medium. As a result of this, the structure of a smoke gas generator is of very simple design, as a result of which additional means for the development of smoke gas are superfluous.

Finally, it is proposed that the smoke gas generator exhibits a capillary device. For example, one end of the capillary tube is arranged in a housing in which the test medium is located. The other end of the capillary tube, by contrast, exhibits a heating device or is in direct operational contact with the heating device. As a result of the capillary tube, adhesion forces always cause a part of the test medium to move in the area of the heating device, which on activation provides for the smoke evaporation of the test medium.

For preference the heating device can be remotely controlled, so that it is only switched on when needed. This is the case, for example, if the smoke gas generator according to the invention is arranged in the immediate vicinity of the gas detector.

In order to avoid the over-heating of the test medium, the possibility pertains of limiting the heating duration of the heating device, so that a switch is accordingly required for reactivation of the heating device.

A further solution to the problem of the invention makes provision for a gas generator, in particular a gas generator for the simulation of a real smoke gas, to be equipped with a collection device for the smoke gas which is generated, whereby the collection device exhibits at least one means for closing. A collection device for the smoke gas which is generated is therefore advantageous, because the gas generator, due among other things to its restricted structural size, is rarely in a position to produce so much smoke gas in a short period of time, with the result that the volume of smoke gas produced is in most cases not sufficient to activate a gas detector. If the gas generator now comprises a collection device, the smoke gas produced will be collected in this, for example, over an extended period of time, and only released in a procedure after a specific period of time.

In order for the smoke gas to be retained in the collection device for as long as required until a sufficiently large volume has been produced, the collection device requires at least one means to close it. This is, for example, a straightforward flap or a valve or the like. It is not mandatorily required in this case for the means for closing the collection device to close with a 100% tight seal.

It is to advantage if the means for closing exhibit a wire, the design of which is temperature-dependent. By means of such a wire it is possible, for example, to actuate the flap in such a way that the collection device closes or at least partially opens respectively. In this situation the wire is for preference of such a design that it can be shortened or lengthened respectively by an electrical current and the temperature increase associated with this.

It is of particular advantage if the means for closing exhibit a Nitiuol wire. The Nitiuol wire contracts, for example, when 2.5 Volts flows through it, as a consequence of the resultant heating, and then expands accordingly when it cools down again. In this situation the contraction of the wire can be used to open the flap.

It is understood that, as an alternative to this, any other actuating element or, for example, even a linear motor can be used.

According to the invention it is further proposed that the collecting device exhibit a smoke inlet aperture. By means of this smoke inlet aperture it is possible for smoke which is generated to pass, for example, from the heat chamber of the gas generator into the collecting device.

A preferred embodiment variant makes provision for the collecting device to exhibit at least one inlet aperture and/o at least one outlet aperture.

The terms "inlet aperture" and "outlet aperture" respectively are understood in this situation to mean that aperture through which, for example, a volume flow can pass into and out of the collecting device. The inlet aperture and the outlet aperture guarantee that the smoke gas can pass out of the collecting device due to an under-pressure or by means of an additional gas. It is also possible for an over-pressure to be established briefly in the collecting device, which "shoots out" the smoke gas from the collecting device.

For preference an air volume flows thorough the inlet and outlet aperture respectively.

It is to particular advantage if the collecting device exhibits a gas detector. In order, for example, to check the gas detector with regard to smoke gas development, it is to advantage if the corresponding gas detector is arranged directly in the collecting device of the gas generator. For example, the inlet aperture and the outlet aperture are open in normal operation so that an air volume which circulates in an air-conditioning system, for example, flows at least in part through the collecting device. As a result of this, it is guaranteed, among other things, that the gas detector in normal operation also has the air flow or a part of the air flow passing through it.

The term "normal operation" is understood to mean in this context, for example, a stationary operation of a system without a fault incident.

In order now to check the gas detector, the inlet aperture and the outlet aperture are closed in accordance with the techniques described heretofore (flap, valve), so that a smoke gas generated by the gas generator cannot escape from the collecting device and therefore come in direct contact with the gas detector. After a successful check of the gas detector, the inlet aperture and the outlet aperture of the collecting device are cleared again, so that the collecting device is blown clear by the air volume flow.

An advantageous further embodiment of the invention makes provision for the collecting device to exhibit a tube. The tube is, for example, of such a design it can be located at a venting channel, whereby a part of the volume flow passing through the venting channel flows through the tube arranged in the venting channel. In this situation, the tube forms a "bypass" to the actual venting channel. This is especially well-suited for the subsequent equipping of a venting channel with a fire detection system.

It is of particular advantage if the collecting device exhibits a changing cross-section. As a result of the changing cross-section, for example, different pressures and flow volumes take effect inside the collecting device, which can have a positive effect on the dissemination of the smoke gas.

An especially simple structural variant makes provision for the collecting device to exhibit a diffusor. By means of the diffusor, different flow velocities and different pressures can be incurred in the collecting device and in the tube respectively.

A preferred embodiment makes provision for the collecting device to exhibit a Venturi nozzle. By means of the Venturi nozzle different pressures and flow velocities can likewise be specifically achieved and put to use in the collecting device.

It is particularly advantageous if the gas generator is arranged in the area of the broadening of the cross-section. The broadening of the cross-section has the effect in general of reducing the flow velocity and a reduction of the pressure at the location of the broadening of the cross-section. If a gas generator is arranged in such an area or in the vicinity of such a broadening of the cross-section, this has an advantageous effect in particular on the expansion of smoke gas inside the collecting device.

It is further proposed according to the invention that the gas generator be arranged in a venting channel. At this location a smoke gas can be generated to particularly good effect.

It is likewise proposed according to the invention that the gas detector be arranged in a venting channel.

The arrangement of the gas generator and/or gas detector in the venting channel can be designed especially easily in respect of the structure, as well as in a particularly space-saving manner.

The problem on which the invention is based is further resolved by a method for testing a gas detector, in which at least one gas generator arranged decentrally is activated by means of a central monitoring device. As a result of the activation, the gas generator produces a gas, for preference a smoke gas, which is detected by the gas detector. In this situation, the gas detector is activated, and issues an appropriate data signal.

The term "monitoring device is understood to mean, for example, a central device in a building in which the safety-relevant functions of the building are monitored.

It is of particular advantage in this situation if a gas detector is not tested directly on the spot, and therefore needs to be activated, but can instead be tested and activated in a simple manner from a central device.

A preferred variant of the method makes provision for the gas detector to pass the data signal to the central monitoring device and/or to an emergency facility. The central monitoring device is located, for example, directly in a building, so that all the steps necessary for the test can be coordinated from there.

It is also to advantage if the data signal is transferred additionally or exclusively to an emergency facility. An emergency facility is, for example, a local fire station or another rescue service.

If the data signal is sent in parallel to the central monitoring device as well as to the emergency facility, it is to advantage if a message about the pending test is sent to the emergency facility before the test itself. For example, the message can contain data regarding on which date and at what time the test will take place, as well as regarding the nature of the test and its duration. For preference the emergency facility is informed automatically by the central monitoring device.

It is proposed according to the invention that at least one signal line is deactivated between the central monitoring device and the emergency facility and/or at least one signal line between at least one gas detector and the emergency facility. In order for the emergency facility, e.g. the fire brigade, not to be brought unintentionally into an alarm status, it is to advantage if the data line to this emergency facility is at least temporarily deactivated.

Finally, it is proposed that a test report be sent to the emergency facility. Once the test has been concluded it is to advantage if the emergency facility is notified, for example, of the current status of the gas detectors of a building.

The problem of the invention is likewise resolved by a method for testing a smoke gas detector in which a smoke gas generator arranged in the vicinity of the smoke gas detector creates a smoke gas by means of a test medium, and the smoke gas initiates a test of a smoke gas detector, whereby the test medium is caused to evaporate in smoke by an electrical heating device. The smoke gas is in this case conveyed by an electrical blower to the smoke gas detector, whereby, after the test has been initiated, the smoke gas detector is vented by means of the blower. It is to advantage with this process if, according to the invention, the smoke gas is generated by an electrical heating device, in that a test medium is caused to evaporate in smoke by the electrical heating device. In this situation the fact is of particular advantage that only a very small quantity of a test medium is consumed for the production of the smoke gas.

The fact is also to advantage that the smoke gas is blown by an electrical blower of the smoke gas generator directly into or at the smoke gas detector, so that a specific smoke application to the smoke gas detector takes place, whereby, among other things the purposefulness of the method causes the effectiveness of a smoke gas detection test to be substantially increased.

Once the test frequency of the smoke gas detector has been successfully initiated, it is to particular advantage if the smoke gas detector is re-vented immediately after the application of the smoke, so that the test is terminated as quickly as possible. As a result of the specific re-venting by means of the smoke gas generator according to the invention, the risk of an undesirable depositing of smoke gas particles in the smoke gas detector will be reduced.

It is understood that the gas generators and heat generators described heretofore, in particular the smoke gas generators, with all their features described, can to advantage be arranged not only as stationary, but can likewise be used as mobile units. To do this it is only necessary for them to be inserted into an appropriate testing device.

Figure 10:
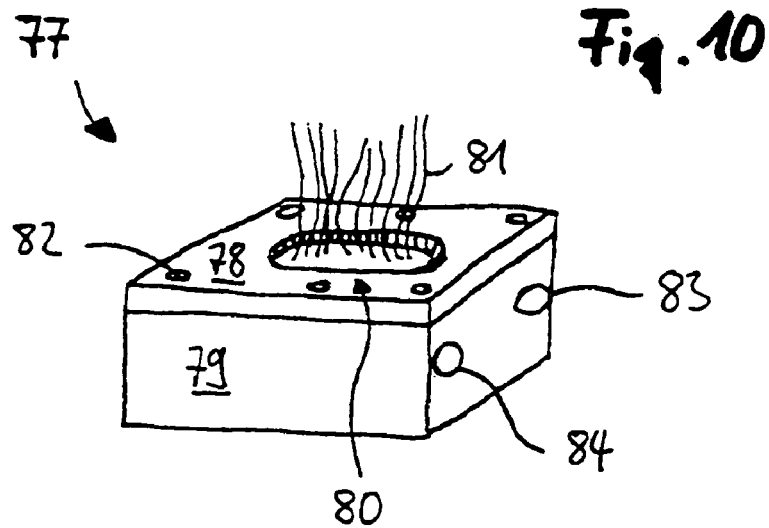
Figure 11:
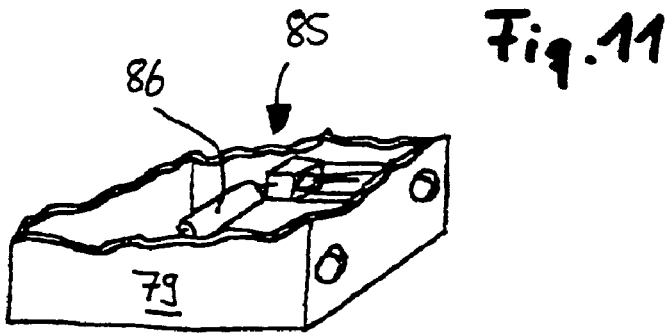
Figure 12:
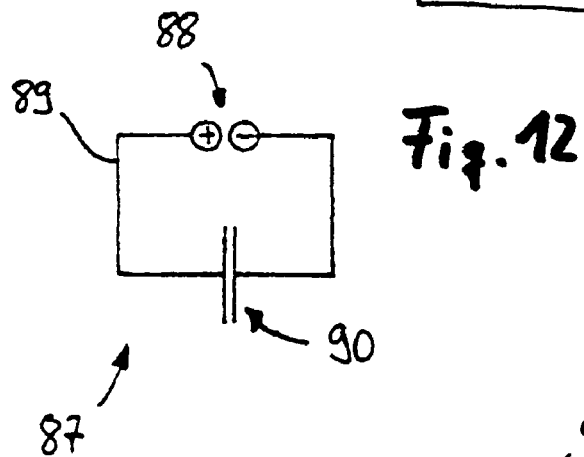
Figure 13:
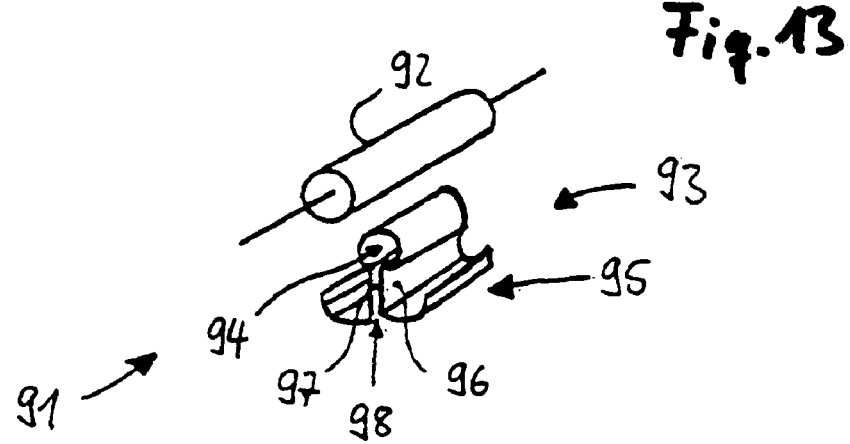
Figure 14:
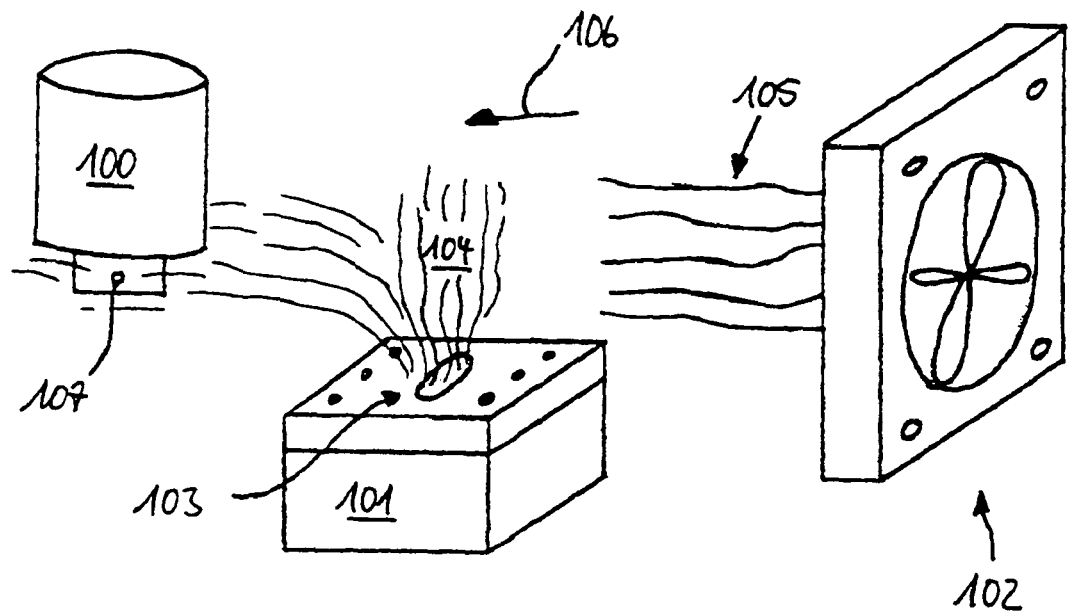
Figure 15:
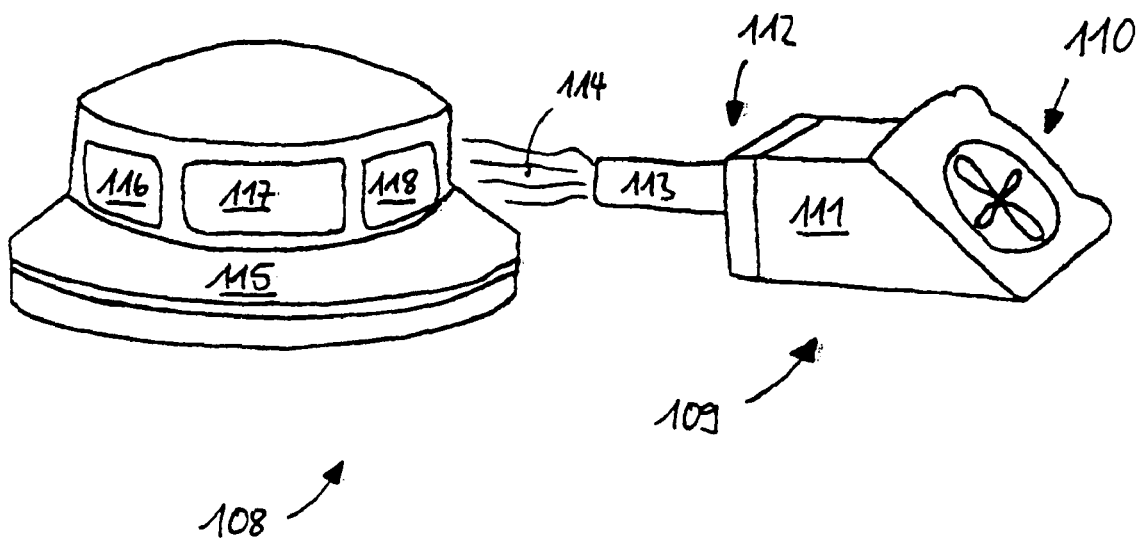

An embodiment of a smoke gas detecting system according to the invention and embodiment examples of different smoke gas generators are represented in the drawings and are explained in greater detail hereinafter. The drawings show:

FIG. 1 A smoke gas detection system consisting of smoke gas detector and smoke gas generator;

FIG. 2 A smoke gas generator with a heatable and wettable rod;

FIG. 3 A smoke gas generator with a heatable capillary tube;

FIG. 4 A smoke gas generator with smoke cartridges;

FIG. 5 A smoke gas generator with a fluid spray container;

FIGS. 6 to 9 Widely differing embodiments of heat detectors and corresponding heat generators;

FIG. 10 A two-part heat chamber;

FIG. 11 A heat chamber shown in part section;

FIG. 12 An accumulator power source shown in diagrammatic form;

FIG. 13 A resistor and a sleeve with capillary surfaces;

FIG. 14 A diagrammatic representation of a smoke gas generator according to the invention;

FIG. 15 An alternative smoke gas generator in reciprocal effect with a smoke gas detector;

FIGS. 16 and 17 A smoke gas detector in a venting channel

Figure 19:
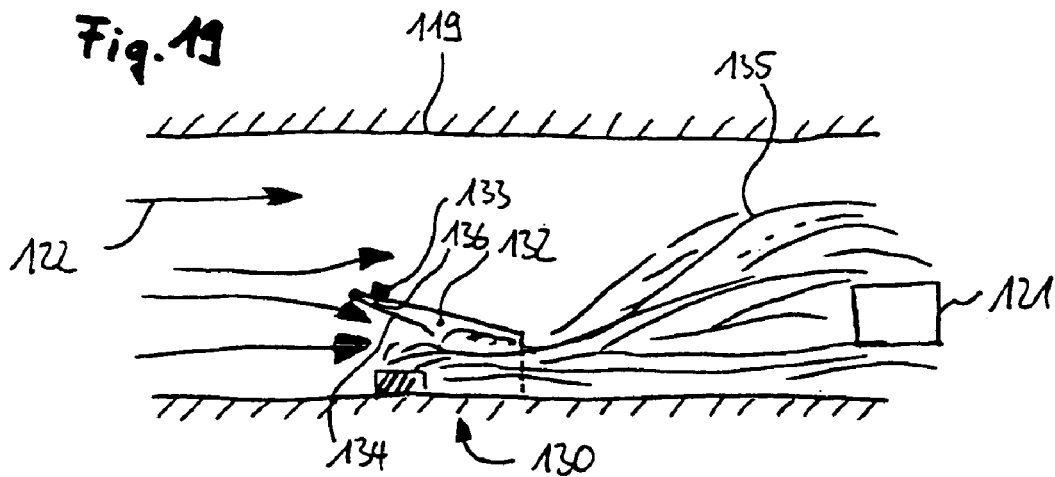

FIGS. 18 and 19 An alternative smoke gas detector in a venting channel

Figure 20:
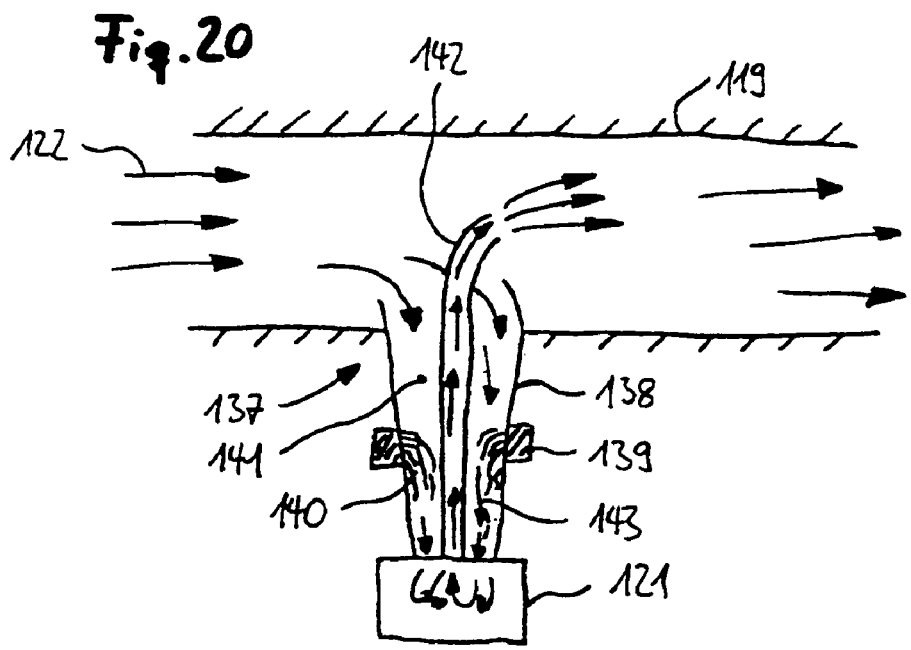

FIG. 20 A further smoke gas detector in a bypass of a venting channel

Figure 21:
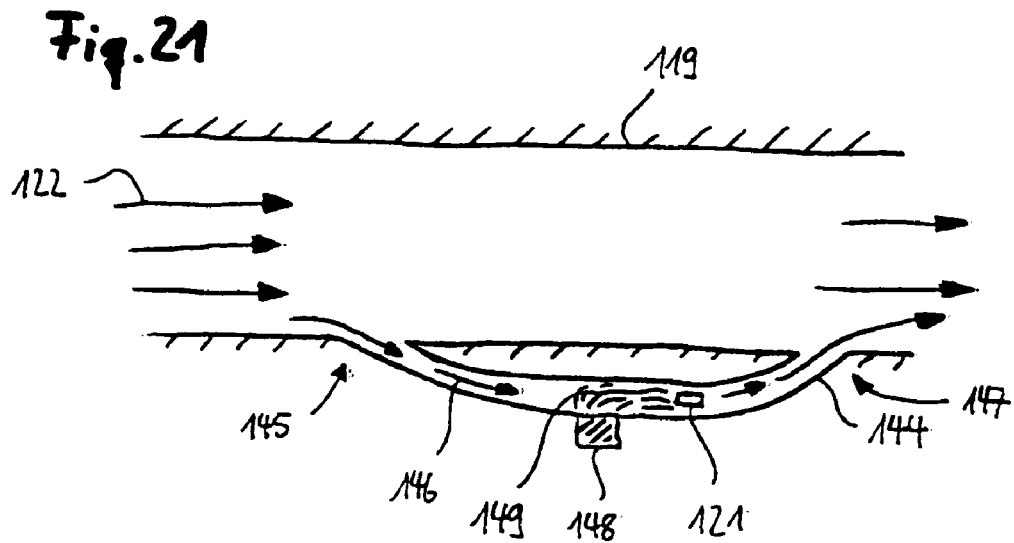

FIG. 21 A smoke gas detector in an alternative bypass of a venting channel; and

Figure 22:
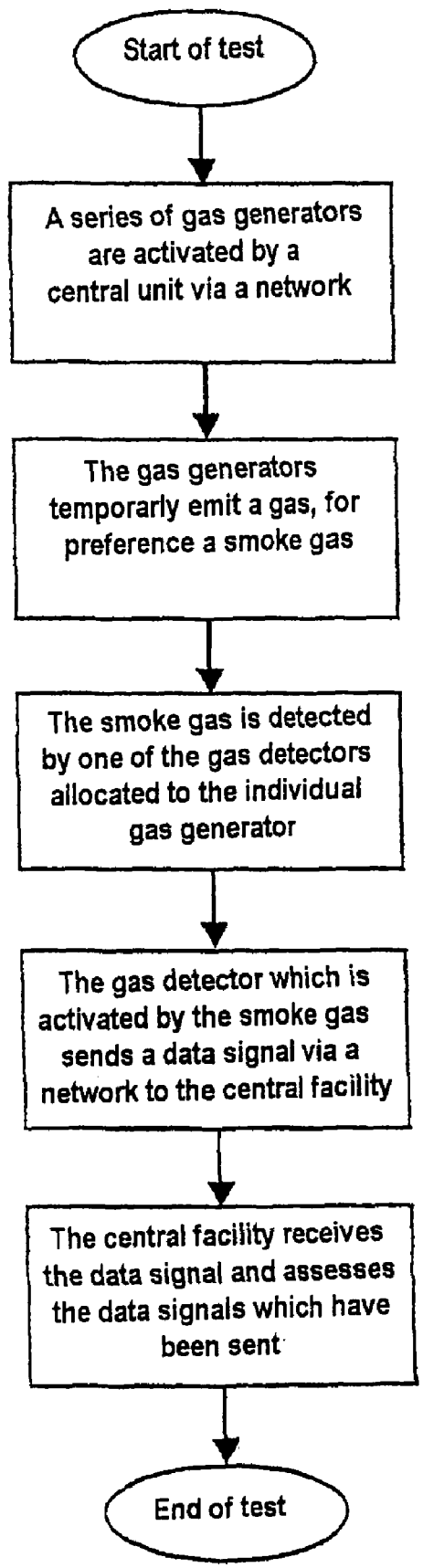

FIG. 22 A method for the testing of at least one gas detector.

The smoke gas detection system 1 represented in FIG. 1 consists of the transmitter 2, the smoke gas generator 3, and the smoke gas detector 4. Also shown is a battery 3a with a lead. In this arrangement, the smoke gas generator 3 and the smoke gas detector 4 are fixed to one another in such a way that they are in an operational connection with one another.

The transmitter 2 consists of a timer 5 and a transmitter device 6. The timer 5 therefore allows for the transmitter system 6 to be actuated at specific predetermined times, such as, for example, each month, so that it issues a signal 7. This signal 7 is picked up by the antenna 8 of the smoke gas generator, and the receiver system 9 causes the valve 10 to open, so that smoke gas is released from the reservoir. The smoke gas cloud 12 which is caused in this process expands and is detected by the detector 4 arranged in the vicinity. In the event of detection, the detector 4 causes an LED 13 to flash and issues a control signal via the line 14. By means of this control signal it is possible, for example, for a roller door to be closed or for a sprinkler system to be switched on.

The transmitter system 2 is arranged so as to be easily accessible, so that it can also be actuated manually. The smoke gas generator 3 and the smoke gas detector 4 are arranged for preference in the ceiling area of buildings, close to one another, so that it is ensured that the smoke gas cloud 12 will be detected by the smoke gas detector 4.

Depending on the application situation, instead of a smoke gas, any other gas can be generated in order to test a suitable gas detector 4 for its effectiveness.

FIGS. 2 to 5 show different embodiment examples of gas generators.

The smoke gas generator 20 shown in FIG. 2 consists of a fluid reservoir 21, into which a rod 22 is immersed. The rod 22 is mounted so as to be rotatable according to the arrow 23, so that it can be pivoted through 45° into the position represented by the dotted line when a radio signal is detected by the receiver 24. Due to the pivoting of the rod 22 the rod 22 is connected to the current source in such a way that it becomes heated and the fluid adhering to it is evaporated. The smoke gas cloud 25 which is thereby engendered is blown by the blower 26 in the direction of the smoke detector (not shown).

An alternative embodiment of a smoke gas generator 30 is represented in FIG. 3. With this smoke gas generator, fluid 33 is sucked out of a reservoir 31 by means of a capillary tube 32. The receiver 34 has the effect that, when a signal is received, current flows through the heating coil 35 and causes the evaporation of a part of the fluid 33 which is sucked up. The blower 36 ensures that the smoke gas cloud 37 which is created is then blown towards a detector (not shown).

FIG. 4 shows a gas generator 40, which allows for two different types of gas to be released. To this effect, two gas cylinders 41, 42 are provided for, the outlets of which exhibit valves 43, 44, which are opened by the receiver 45 depending on the signal received. As a result a gas cloud 46 is formed, which can be detected by a detector (not shown). This smoke gas generator therefore makes it possible to test whether the detector also responds to different types of gas.

A further embodiment of a smoke gas generator 50 is shown in FIG. 5. With this device a pressure vessel 52 is provided for, filled with a fluid 51. A gas buffer 53 under pressure ensures that, when the valve 54 is opened, a spray jet 55 is released. This spray jet strikes a heated surface 56, so that the sprayed fluid evaporates and creates a gas cloud 57. A receiver 58 is connected to the valve 54 in such a way that when a signal is received the valve 54 opens and a spray jet strikes the plate 56 and evaporates there. The blower 59 blows the gas cloud 57 to a detector (not shown) in order to actuate the signal there.

The embodiments shown demonstrate that different gas generators are possible in order to generate a gas in a simple manner which can be detected by a gas detector in order to initiate a signal. The person skilled in the art will recognise that the possibilities for smoke gas generation are not restricted to the embodiments described.

The heat detector 60 represented in FIG. 6 is arranged on the ceiling of a building 61 and forms a physical unit with a heat generator 62, which is represented in the form of a metal wire 62. If it is intended that the heat detector 60 should now be tested, an electric current is conducted through the metal wire 62, whereby the metal wire 62 is heated and the heat generated is sufficient to activate the heat detector 60.

Figure 7:
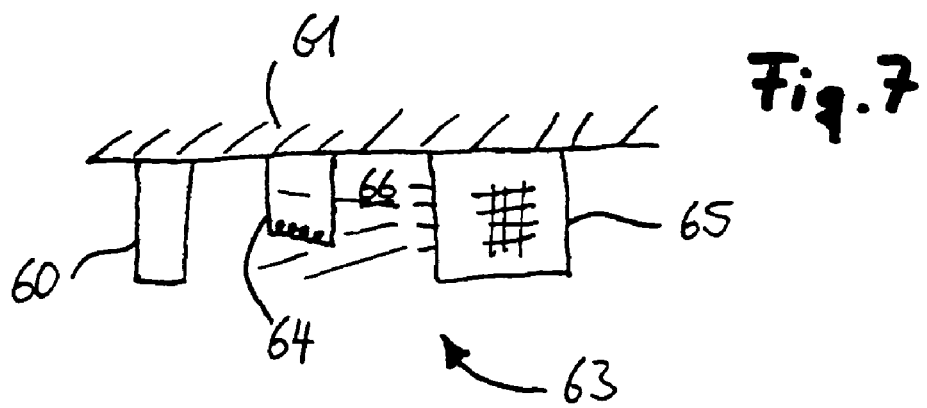
Figure 8:
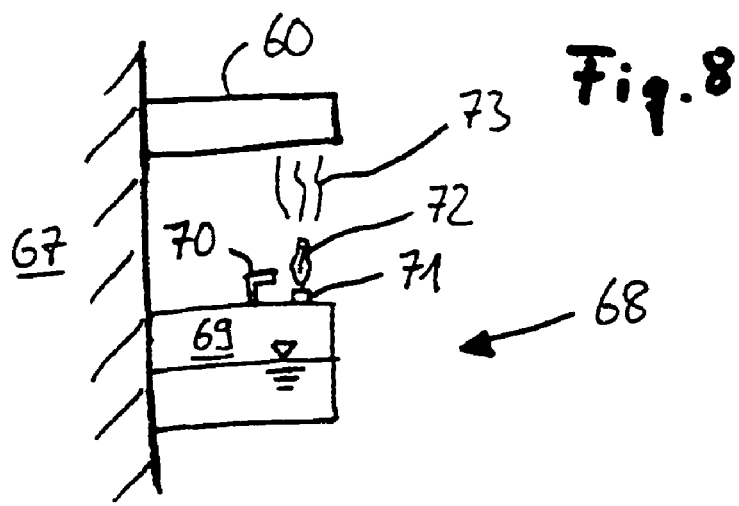
Figure 9:
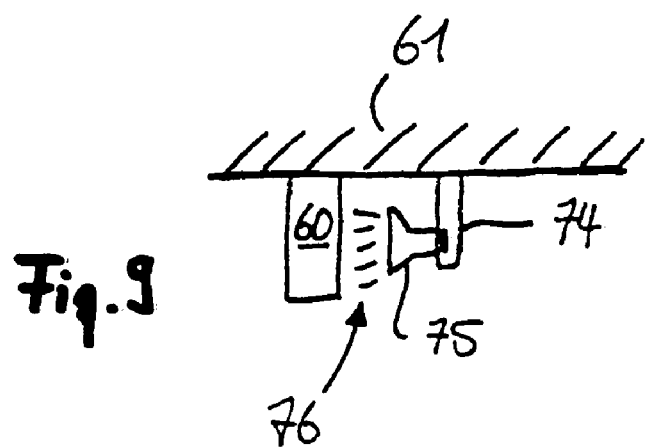

The heat detector 60 shown in FIG. 7 is likewise arranged on the ceiling 61. Arranged in the vicinity of the heat detector 60 is a heat generating system 63, whereby the heat generating system 63 consists of a heating coil 64 and a blower unit 65. During a test of the heat detector 60 the incandescent coil 64 is activated, so that the incandescent coil 64 generates heat. This heat is then transferred by means of the blower unit 65 and an air flow 66 to the heat detector, such that this detects the heat.

It is likewise possible for the heat detector 60 to be arranged on a vertical surface 67. Located beneath the heat detector 60 is a heat generator 68, whereby the heat generator 68 exhibits a fluid container 69 and an ignition device 70. In this situation, a combustible medium flows through a nozzle 71, said medium being ignited by the ignition device 70, so that a flame 72 develops heat 73, whereby the rising heat 73 actuates the heat detector 60.

In a further embodiment, the heat detector 60 is in turn arranged at the ceiling 61. Arranged in the immediate vicinity of the heat detector 60 is a heat generator 74. The heat generator 74 exhibits a heat radiator unit 75 in the form of an infra-red lamp. If the infra-red lamp is activated, it generates a radiant heat 76, which activates the heat detector 60.

It is understood that the possibilities described heretofore in respect of a heat detector and heat generator are not restricted to the embodiments indicated, but that a large number of other embodiments can pertain. It follows from this that the invention can be applied to any desired heat detector in which provision is made for an appropriate heat generator. In this situation the heat detector and the heat generator are either fixed to one another in such a way that they are in an operational connection to one another, or the heat generator forms a physical unit with the heat detector.

The two-part heat chamber 77 represented in FIG. 10 exhibits a closure cover 78 and a basic housing 79. The closure cover 78 has in its centre an opening 80, through which a generated smoke gas 81 rises. In addition to this, the closure cover 78 is screwed to the basic housing 79 by a large number of screws. The basic housing 79 has two holes 83 and 84 in its sides, which accommodate plug contacts for an electrical connection (not shown here).

Arranged in the interior of the basic housing 79 is a heating device 85, whereby the heating device 85 exhibits a resistor 86.

Shown in FIG. 12 is the straightforward design of an electrical circuit 87 of the smoke gas generator according to the invention. In this case, an accumulator 88 serves as the current source, which is connected by means of a wire connection 89 to a heat conducting body 90 (capacitor, Ohmic resistor).

The arrangement 91 of FIG. 13 shows an Ohmic resistor 92 and a capillary sleeve 93. The external diameter of the Ohmic resistor 92 corresponds approximately to the inner diameter of the capillary sleeve 93. In an area 94, with its lower area 95, the capillary sleeve 93 is arranged in a gel-type test medium (not shown here), whereby the gel-type test medium moves in the inner area between the capillary surfaces 96 and 97 by means of capillary forces in the direction of the arrow 98 between the two capillary inner surfaces 96 and 97 to the Ohmic resistor 92.

An arrangement 99 of FIG. 14 comprises a smoke gas detector 100, a heat chamber 101, and a fan 102. A smoke gas 104 passes through an aperture 103 of the heat chamber 101 into the immediate surrounding area of the arrangement 99. The fan 102 blows an air flow 105 in the direction of the arrow 106. In this situation the smoke gas 104 is conducted together with the air flow 105 and is registered by a detector 107 of the smoke gas detector 100, as a result of which an alarm signal is injected.

Once the test of the smoke gas detector 100 has been concluded, the development of the smoke gas 104 in the heat chamber 101 is suppressed, in that the electrical heating device 85 is switched off. The air flow 105 from the fan 102 blows the smoke gas detector 100, in particular the detector 107 of the smoke gas detector 100, free of the remaining smoke gas particles of the smoke gas 104.

In the embodiment 108, a smoke gas generator 109 and a fan 110 are arranged together in a housing 111. The housing 111 exhibits in its front area 112 a tube 113, through which a smoke gas 114, generated by the smoke gas generator 109, is blown by the fan 110. The housing 111 in this situation is arranged relative to a smoke gas detector 114 in such a way that the smoke gas 114 passes directly via apertures 116, 117 and 118 to the detector of the smoke gas detector 115. By means of the tube 113 a specifically-directed flow to the smoke gas detector 115 by smoke gas 114 from the smoke gas generator 109 is easily possible.

The venting channel 119 of FIGS. 16 to 19 exhibits a smoke gas generator 120 and a smoke gas detector 121. The smoke gas generator 120 and the smoke gas detector 121 are in each case arranged behind one another on the mid-axis of the venting channel 119. A volume of air 122 flows through the venting channel 119. The volume of air 122 first impinges on the smoke gas generator 120 and then on the smoke gas detector 121.

The smoke gas generator 120 comprises a smoke gas collecting chamber 123, which is not closed on the side 124 turned away from the smoke gas detector 121. On the side 125 turned towards the smoke gas detector 121, the smoke gas collecting chamber 123 exhibits a closure element 126. Located in the area of the closure element 126 is a closure element 127, which makes it possible, for preference by means of an electric pulse, for the flap 126 to be opened.

If it is now intended that the smoke gas detector 121 should be tested, the smoke gas generator is activated, so that it produces a smoke gas 128. This smoke gas 128 collects in the smoke gas collecting chamber 123 until the flap 126 is opened by means of the closure element 127, and a concentrated draught of smoke 129 escapes from the smoke collecting chamber 123 in the direction of the smoke gas detector 121. The draught of smoke 129 is drawn along with the volume flow 122 through the venting channel 119.

According to the invention, such a volume of smoke gas 128 can gather in the smoke gas collecting chamber 123 over a sufficiently long period of time, so that the collected smoke gas 128 has the effect of causing such a strong draught of smoke gas 129 into the venting channel 119 that the detectors of the smoke gas detector 121 respond to the smoke gas draught 129.

Arranged in the venting channel 119 of FIGS. 18 and 19 is an alternative smoke gas generator 130, which, if required, has a reciprocal effect on the smoke gas detector 121. The smoke gas detector 130 in this embodiment is not arranged on the mid-axis of the venting channel 119, but on the inner side 131. The alternative smoke gas detector likewise comprises a somewhat larger cavity than the smoke gas collecting chamber 132 in which a corresponding smoke gas gathers when the smoke gas generator 130 is activated. If sufficient smoke gas is collected in the smoke gas collecting chamber 132, a flap 134 of the smoke gas detector 130 is opened by means of a closure element 133, so that a volume flow 122 can at least in part flow through the smoke gas collecting chamber 132, and thereby carry the smoke gas to a smoke gas pan 135 at the smoke gas detector 121. The closure element 133 is electrically actuated in this situation, whereby a Nitiuol wire 136 contracts and the flap 134 opens.

The venting channel 119 represented in FIG. 20 exhibits in one area a passage aperture 137. Arranged at the passage aperture 137 is a first tube 138, which forms a connection between the venting channel 119 and a smoke gas detector 121. Arranged on the outer tube 138 is a smoke gas generator 139, which if required can create a smoke gas 140. In the interior 141 of the first outer tube 138 is a further tube 142, which likewise forms a connection between the venting channel 119 and the smoke gas detector 121.

A volume of air 122 flows through the venting channel 119. The volume of air 123 is conducted partially through the interior 141 of the tube 138 to the smoke gas detector 121. From there the volume of air conducted through the first outer tube 138 passes via the second outer tube 142 back into the venting channel again. Because a part of the volume of air 122 is now always being conducted through the smoke gas detector 121 via the two tubes 138 and 142, the smoke gas detector is in a position to generate a signal when a smoke gas 140 is present in the volume of air 122.

If it is now intended that the smoke gas detector 121 should be inspected, the smoke gas generator 139 is adjusted in such a way that a smoke gas 140 is generated. This smoke gas 140 is now conducted by a part volume 143 of the volume of air 122 via the outer first tube 138 to the smoke gas detector 121. This is now in a position to detect the smoke gas 140 and generate a corresponding signal, which indicates the presence of smoke gas 140.

The venting channel 119 of FIG. 21 exhibits a bypass 144. The bypass 144 has an inlet aperture 145, which allows a part volume flow 146 of the volume flow 122 to enter into the bypass 144, and an outlet area 147, through which the part volume flow 146 can flow back again into the venting channel 119. The bypass 144 additionally exhibits a smoke gas generator 148 and a smoke gas detector 121. The bypass is further designed in such a way that it exhibits a larger cross-section in the area of the smoke gas generator 148 than in the area of the inlet aperture 145. As a result of this, the flow velocity of the part volume flow 146 is reduced in the area of the smoke gas generator 148, as a result of which an under-pressure occurs in this area. The effect of this is that a smoke gas 149 created by the smoke gas generator 148 is drawn into the bypass 144, and is carried with the part volume flow 146 to the smoke gas generator 121.

The bypass 144 is arranged according to the invention at the venting channel 119 in such a way that a part volume flow 146 of the volume flow 122 always flows through it. If the volume flow 122 is carrying a smoke gas with it, this passes via the bypass 144 to the smoke gas detector 121, which then initiates an appropriate signal. If, by contrast, a smoke gas 149 is only simulated, in order to check the smoke gas detector 121 for functional performance, the smoke gas 149 is created by means of the smoke gas generator 148, and carried with the part volume flow 146 to the smoke gas detector 121.

The process sequence represented in FIG. 22 begins with the start of the test, whereby a series of gas generators are activated by means of a central facility via a network. The activated gas generators thereupon at least temporarily emit a gas, whereby the gas is for preference a smoke gas. The smoke gas in this situation is conducted to the gas detector in such a way that the smoke gas is detected by a gas detector allocated to the individual gas generator. The gas detector activated by the smoke gas issues a data signal via a network to the central facility. The issue of the data signal indicates that the gas generator is functioning correctly and is responding to the smoke gas. The central facility -which receives the data signal assesses the data signals being issued. This then brings the test to an end.

If a data signal from a gas detector does not reach the central facility as provided for, the gas detector and the gas generator are checked manually.

As an alternative to the procedure described heretofore it is possible for a data signal to be sent, in parallel to the central facility, also to a further facility. This facility is, for example, a fire station. If such a direct connection to the fire brigade pertains, then it is to advantage if the fire brigade are informed, for preference automatically, by the central facility about the time schedule and sequence of the test. It is possible, if appropriate, for the central facility to deactivate the direct data line to the fire brigade temporarily, so that the fire brigade are not sent a data signal during the test, and therefore, for example, the risk of a false alarm is avoided.

After the test, the direct data connection to the fire brigade is for preference automatically re-established.

The invention is explained on the basis of a smoke gas generator and a smoke gas detector. It can, however, be applied to any desired gas detector or heat detector by making provision for, an appropriate gas generator or heat generator.

The invention claimed is:

1. A test system for use with a detection system comprising a detector for detecting the presence of a gas and/or combustion product, the detector comprising a housing having at least one aperture for receiving the gas and/or combustion product therethrough, the test system comprising:
    a testing device for testing the detector, the testing device comprising a source of test medium, a heating means for heating the test medium in order to generate test stimulus representative of the gas or combustion product, means for supplying the test medium to the heating means from the source;
    and means for supplying the test stimulus to the detector,
    wherein the testing device is mounted in a fixed and permanent position relative to the detector even while the detector is not undergoing a test,
    wherein the means for supplying the test stimulus to the detector comprises a fan blower for directing the flow of the stimulus from the testing device to the detector during a test, and
    wherein the fan blower is capable of being switched off while the detector is operating to detect the presence of the gas or combustion product.

2. The system of claim 1 wherein the testing device is fixed to the detector such that the testing device and detector are in operational connection with one another.

3. The system of claim 1 wherein the means for supplying the test stimulus to the detector further comprises a tubing for directing the flow of stimulus from the testing device to the detector.

4. The system of claim 1 wherein the test medium is a liquid, gel, or solid.

5. The system of claim 1 wherein the test medium comprises a material which is transformed into the test stimulus when heated.

6. The system of claim 1 wherein the heating means is electrically operated.

7. The system of claim 1 wherein the fan blower is arranged to continue to blow air towards the direction of the detector after supplying the stimulus to the detector.

8. The system of claim 1 wherein the testing device further comprises a battery or rechargeable battery to provide power to the device.

9. The system of claim 1 further comprising a power supply means for supplying power from an electrical power distribution system or from a low voltage power source.

10. The system of claim 1 further comprising a control means for controlling the activation and deactivation of the testing device.

11. The system of claim 10 wherein the control means is in wired communication with the testing device.

12. The system of claim 10 wherein the control means is positioned remote from the testing device and is arranged to control the activation and deactivation of the testing device via wireless communication.

13. The system of claim 1 wherein the testing device comprises a heating chamber comprising on one side thereof a blocking member arranged to prevent stimulus generated by the testing device to be directed towards the detector when the blocking member is in the closed position.

14. The system of claim 13 wherein the heating chamber further comprises a closure element arranged to control the position of the blocking member.

15. A gas and/or combustion product detection system comprising a gas and/or combustion product detector and a testing device mounted in a fixed and permanent position relative to the detector even while the detector is not undergoing a test, the detector comprising a housing having at least one aperture for receiving the gas and/or combustion product therethrough, the testing device comprising:
a source of test medium;
a heating means for heating the test medium in order to generate test stimulus representative of the gas and/or combustion product;
means for supplying the test medium to the heating means from the source; and
means for supplying the test stimulus to the detector,
wherein the means for supplying the test stimulus to the detector comprises a fan blower for directing the flow of the stimulus from the testing device to the detector during a test, and
wherein the fan blower is capable of being switched off while the detector is operating to detect the presence of the gas or combustion product.

16. The system of claim 15 wherein the testing device is fixed to the detector such that the testing device and detector are in operational connection with one another.

17. The system of claim 15 wherein the means for supplying the test stimulus to the detector further comprises a tubing for directing the flow of stimulus from the testing device to the detector.

18. The system of claim 15 wherein the test medium is a liquid, gel, or solid.

19. The system of claim 15 wherein the test medium comprises a material which is transformed into the test stimulus when heated.

20. The system of claim 15 wherein the heating means is electrically operated.

21. The system of claim 15 wherein the fan blower is arranged to continue to blow air towards the direction of the detector after supplying the stimulus to the detector.

22. The system of claim 15 wherein the testing device further comprises a battery or rechargeable battery to provide power to the device.

23. The system of claim 15 further comprising a power supply means for supplying power from an electrical power distribution system or from a low voltage power source.

24. The system of claim 15 further comprising a control means for controlling the activation and deactivation of the testing device.

25. The system of claim 24 wherein the control means is in wired communication with the testing device.

26. The system of claim 24 wherein the control means is positioned remote from the testing device and is arranged to control the activation and deactivation of the testing device via wireless communication.

27. The system of claim 15 wherein the testing device comprises a heating chamber comprising on one side thereof a blocking member arranged to prevent stimulus generated by the testing device to be directed towards the detector when the blocking member is in the closed position.

28. The system of claim 27 wherein the heating chamber further comprises a closure element arranged to control the position of the blocking member.

29. A conduit or pipe based detection system for a gas and/or combustion product comprising:
an elongate conduit;
a detector for detecting the presence of the gas and/or combustion product in the conduit, the detector comprising a housing having at least one aperture for receiving the gas and/or combustion product therethrough; and
a testing device for testing the detector and comprising:
a source of test medium;
a heating means for heating the test medium in order to generate test stimulus representative of the gas and/or combustion product;
means for supplying the test medium to the heating means from the source; and
means for supplying the test stimulus to the detector,
wherein the testing device is positioned on, in or near the conduit in a fixed and permanent position relative to the detector even while the detector is not undergoing a test,
wherein the means for supplying the test stimulus to the detector comprises a fan blower for directing the flow of the stimulus from the testing device to the detector during a test, and
wherein the fan blower is capable of being switched off while the detector is operating to detect the presence of the gas or combustion product.

30. The system of claim 29 wherein both the detector and testing device are positioned in the elongate conduit.

31. The system of claim 29 wherein the testing device is positioned in the elongate conduit.

32. The system of claim 29 wherein the means for supplying the test stimulus to the detector further comprises a tubing for directing the test stimulus into the elongate conduit.

33. The system of claim 29 wherein the testing device comprises a heating chamber comprising on one side thereof a blocking member arranged to prevent stimulus generated by the testing device to be directed towards the detector when the blocking member is in the closed position.

34. The system of claim 33 wherein the heating chamber further comprises a closure element arranged to control the position of the blocking member.

35. A test system for use with a conduit, pipe or duct based detection system comprising a detector for detecting the presence of a gas and/or combustion product, and a conduit, the detector comprising a housing having at least one aperture for receiving the gas and/or combustion product therethrough, the test system comprising:
- a testing device for testing the detector and comprising: means for generating a test stimulus representative of the gas and/or combustion product and a means for supplying the test stimulus to the detector comprising a fan blower for directing the flow of the stimulus from the testing device to the detector during a test;
- wherein the testing device is positioned on, in or near the conduit in a fixed and permanent position upstream of the detector even while the detector is not undergoing a test; and
- wherein the fan blower is capable of being switched off while the detector is operating to detect the presence of the gas or combustion product.

36. The system of claim 35 wherein the detector is connected to the conduit.

37. The system of claim 35 wherein the testing device is connected to the conduit.

38. The system of claim 35 wherein both the detector and testing device are connected to the conduit.

39. The system of claim 35 wherein the testing device is positioned on the outside of the conduit and the means for supplying the test stimulus to the detector further comprises tubing for directing the test stimulus into the conduit.

40. The system of claim 35 further comprising a stimulus generation chamber comprising on one side thereof a blocking member arranged to prevent stimulus generated by the testing device to be provided to the detector when the blocking member is in the closed position.

41. The system of claim 40 wherein the stimulus generation chamber further comprises a flap arranged to control the position of the blocking member.

42. The system of claim 35 further comprising a monitoring unit for controlling operation of the testing device, and for monitoring the detector, wherein the detector is adapted to send a data signal to the monitoring unit when the test stimulus supplied by the testing device is detected by the detector.

43. The system of claim 35 wherein the testing device is adapted to temporarily supply the test stimulus to the conduit.

* * * * *

UNITED STATES PATENT AND TRADEMARK OFFICE
CERTIFICATE OF CORRECTION

| | | |
|---|---|---|
| PATENT NO. | : 7,934,411 B2 | Page 1 of 1 |
| APPLICATION NO. | : 11/142042 | |
| DATED | : May 3, 2011 | |
| INVENTOR(S) | : Koch | |

It is certified that error appears in the above-identified patent and that said Letters Patent is hereby corrected as shown below:

On the cover page, column 1, item [30], please insert the Claim of Priority of the Foreign Application Priority data to read as follows:

-- Sep. 29, 2000 (DE)..................... 100 48 760.2 --.
-- Jan. 30, 2001 (DE)..................... 101 04 330.9 --.
-- April 6, 2001 (DE).....................101 17 469.1 --.
-- May 9, 2001 (DE)..................... 101 22 572.5 --.
-- Aug. 15, 2001 (DE)..................... 101 39 033.5 --.

Signed and Sealed this
Seventh Day of June, 2011

David J. Kappos
*Director of the United States Patent and Trademark Office*